United States Patent [19]

Drivon et al.

[11] Patent Number: 5,532,420
[45] Date of Patent: Jul. 2, 1996

[54] MANUFACTURE OF SOLID PERFLUOROALKYL BROMIDES

[75] Inventors: Gilles Drivon, Saint Martin en Haut; Dominique Bindi, Sainte-Foy-les-Lyon, both of France

[73] Assignee: Elf Atochem S.A., Paris, France

[21] Appl. No.: 304,457

[22] Filed: Sep. 12, 1994

[30] Foreign Application Priority Data

Sep. 16, 1993 [FR] France .................................. 93 11045

[51] Int. Cl.⁶ ..................................... C07C 19/08
[52] U.S. Cl. ............................................. 570/170
[58] Field of Search .................................. 570/174, 170

[56] References Cited

FOREIGN PATENT DOCUMENTS

0450584A1  10/1991  European Pat. Off. .
0515258A1  11/1992  European Pat. Off. .
4116361A1  1/1992  Germany .

*Primary Examiner*—Alan Siegel
*Attorney, Agent, or Firm*—Spencer & Frank

[57] ABSTRACT

This invention relates to manufacture a normally solid perfluoroalkyl bromide by thermalbromination in the gas phase of a $C_{10}$ or greater perfluoroalkyl iodide, bromination is carried out in the presence of a normally liquid perfluoroalkyl bromide.

This makes it possible to carry out the post-treatment operations (reduction of iodine, separation, neutralization/washing, and the like) at room temperature.

21 Claims, No Drawings

MANUFACTURE OF SOLID PERFLUOROALKYL BROMIDES

FIELD OF INVENTION

The present invention relates to the field of perfluoroalkyl bromides and more particularly has as subject the manufacture of perfluoroalkyl bromides which are solid at room temperature, that is to say those in which the linear or branched $C_nF_{2n+1}$ perfluoroalkyl radical contains 10 or more than 10 carbon atoms.

BACKGROUND OF THE INVENTION

Due to their promising development in the medical field as radiopaques (contrast agents for X-rays) or as oxygen carriers in blood substitutes, perfluoroalkyl bromides have formed the subject in recent years of many patents relating to their synthesis from perfluoroalkyl sulphochlorides $R_FSO_2Cl$ (EP 0,298,870 and 0,429,331), from perfluoroalkyl iodides $R_FI$ (JP 85-184033, EP 0,428,039, EP 0,450,584, EP 0,515,258 and EP 0,519,808) or from hydrogenoperfluoroalkanes $R_FH$ (US 3,456,024 and EP 0,549,387) as well as to their purification (EP 0,513,783). The processes described in these patents are essentially targeted at the manufacture of perfluoroalkyl bromides which are liquid at room temperature and in particular at that of n-perfluorooctyl bromide $C_8F_{17}Br$ (known under the abbreviation PFOB).

Among these known processes, the most direct route for obtaining perfluoroalkyl bromides is obviously that described in Patents EP 0,450,584 and 0,515,258 which consists of the thermalbromination in the gas phase of the corresponding iodides $R_FI$ which are available in industrial quantities. An industrial plant for the manufacture of a perfluoroalkyl bromide must comprise, downstream of the reactor, various devices which make it possible to recover the iodine by-product and to isolate the perflUoroalkyl bromide by means of unit operations such as reduction of iodine, neutralization, separation, neutralization/washing, and the like.

When the desired perfluoroalkyl bromide is liquid at room temperature, especially PFOB, the melting point of which is 6° C., these various devices are very simple and inexpensive appliances because they do not need to be traced or to have a double heating jacket.

An industrial plant designed with such equipment for the manufacture of a liquid bromide such as PFOB cannot be used, without significant investment and modification, for manufacturing a solid bromide such as perfluorodecyl bromide (hereinafter PFDB), the melting point of which is 55° C., the starting perfluorodecyl iodide having a melting point of 65° C.

DESCRIPTION OF THE INVENTION

It has now been found that this problem can be solved by carrying out the thermalbromination of a perfluoroalkyl iodide leading to a normally solid bromide in the presence of a normally liquid perfluoroalkyl bromide. Thus, during the various purification operations and up to the final distillation stage, the normally solid bromide is found in a liquid form which is transportable at room temperature.

The process according to the invention for the manufacture of a normally solid perfluoroalkyl bromide by thermalbromination in the gas phase of a perfluoroalkyl iodide containing 10 or more than 10 carbon atoms is thus characterized in that the bromination is carried out in the presence of a normally liquid perfluoroalkyl bromide.

In the expressions "normally solid" and "normally liquid", the term "normally" is understood to mean for room temperature at atmospheric pressure.

It is possible to use, as normally liquid perfluoroalkyl bromide, any bromide containing from 4 to 8 carbon atoms but, industrially, it is preferable to employ perfluorohexyl bromide and, more particularly, perfluorooctyl bromide.

The quantity of normally liquid perfluoroalkyl bromide to be used can vary within wide limits and depends essentially on the respective solubility of the liquid bromide used and of the solid bromide to be produced. This quantity must, in accordance with the invention, be sufficient to keep the bromide to be produced in solution throughout all the post-treatment stages (reduction of iodine, separation, washing, and the like). For the manufacture of PFDB from perfluorodecyl iodide in the presence of PFOB, the initial $C_{10}F_{21}I/PFOB$ ratio by weight can, purely by way of indication, range from 0.01 to 1.5, preferably between 0.1 and 1.

The bromination reaction of the solid perfluoroalkyl iodide containing 10 or more than 10 carbon atoms (hereinafter $R_FI$) can, as in the prior art, be carried out in a tubular reactor at a temperature ranging from 200° to 550° C., preferably between 350° and 450° C. Bromine and a solution of $R_FI$ in the liquid bromide can be supplied separately to the reactor. However, it is preferable to supply the reactor with a homogeneous mixture or a single solution of bromine and $R_FI$ in the normally liquid perfluoroalkyl bromide; this makes it possible to carry out the bromination with a single supply, to ensure a constant $Br_2/R_FI$ molar ratio and, in case of accidental shut-down or of misadjustment of the feed pump, to avoid any risk of formation of very toxic perfluoroisobutylene.

The $Br_2/R_FI$ molar ratio can range from 0.4 to 2 but is preferably between 0.5 and 0.8.

As the reaction of bromine with the $R_FI$ in the gas phase is very rapid, the contact time, that is to say the residence time of the reactants in the reactor, is not a critical parameter. A contact time of between 1 second and 2 minutes is generally well suited but, industrially, it is preferable to carry out the bromination with a contact time ranging from 5 to 60 seconds.

The reactor can be an empty tube made of glass, quartz or Inconel 600, but it can optionally contain a solid inert substrate (for example glass or quartz) in order to facilitate contact between the gases. Although not essential, the bromination can also be carried out in the presence of an inert gas, for example nitrogen.

It is preferable industrially to carry out the bromination at atmospheric pressure but it would not be departing from the scope of the present invention to operate at a pressure slightly less than or greater than atmospheric pressure provided that the reaction system remains in the gaseous state.

At the reactor outlet and after cooling to a temperature between approximately 150° and 250° C., the gases are treated at a temperature of less than 40° C. with an aqueous solution of a reducing agent such as, for example, sodium sulphite, in a quantity sufficient to reduce the iodine formed and the bromine possibly present (unreacted $Br_2$). After separation at room temperature, the lower organic phase is neutralized with an aqueous solution of any alkaline agent and then separated again before distillation at atmospheric pressure or at reduced pressure.

EXAMPLES

The following examples illustrate the invention without limiting it.

EXAMPLE 1

A homogeneous mixture composed of 3021 g of perfluorooctyl bromide $C_8F_{17}Br$, 3021 g of perfluorodecyl iodide $C_{10}F_{21}I$ and 434 g of bromine is prepared and is maintained at a temperature between 25 ° and 40° C.

This mixture is then introduced over 2 hours into a 3-liter Pyrex reactor operating under the following operating conditions:

temperature: 400°±10° C.

contact time: approximately 30 seconds $Br_2/C_{10}F_{21}I$ molar ratio =0.58.

After cooling, the gases exiting from the reactor are treated with 2667 g of an 18% aqueous sodium sulphite solution at 35°–40° C. After separation at room temperature, two phases are obtained:

an upper aqueous phase which is assayed by argentometry in order to determine its bromide and iodide ions content ($Br^-$=0.78 eq and $I^-$=4.62 eq)

a lower organic phase which, after washing at 20° C by means of 400 g of a 2N aqueous sodium hydroxide solution, weighs 5808 g and whose analysis by gas phase chromatography on a Hewlett Packard 5890 apparatus (FID detector; 60 m capillary DB1 column) gives the following composition by weight:

$C_8F_{17}Br$ : 50.54%

$C_{10}F_{21}Br$ : 48.63%

$C_{10}F_{21}I$ : 0.37% which corresponds to a degree of conversion of the $C_{10}F_{21}I$ which is greater than 99% and to a selectivity towards $C_{10}F_{21}Br$ which is greater than 99.5%.

After distillation of the organic phase on a 17-plate Kerapak column, 2240 g of perfluorodecyl bromide (purity ≧ 99.9%) are obtained.

EXAMPLE 2

The reaction is carried out as in Example 1 from a mixture composed of 4903 g of $C_8F_{17}Br$, 1226 g of $C_{10}F_{21}I$ and 187 g of bromine, i.e. a $Br_2/C_{10}F_{21}I$ molar ratio of 0.62. The following results are obtained:

Aqueous phase: $Br^-$=0.46 eq $I^-$=1.89 eg

Organic phase (6003 g) $C_8F_{17}Br$:80.10% $C_{10}F_{21}Br$:19.30% $C_{10}F_{21}I$:0.06% which corresponds to a degree of conversion of the $C_{10}F_{21}I$ which is greater than 99% and to a selectivity towards $C_{10}F_{21}Br$ which is greater than 99.5%.

EXAMPLE 3

The reaction is carried out as in Example 1 but replacing perfluorooctyl bromide with perfluorohexyl bromide $C_6F_{13}Br$. A mixture composed of 2653 g of $C_6F_{13}Br$, 2653 g of $C_{10}F_{21}I$ and 390 g of bromine, i.e. a $Br_2/C_{10}F_{21}I$ molar ratio equal to 0.59, is used.

Analysis of the aqueous and organic phases gives the following results:

Aqueous phase: $Br^-$=0.77 eq $I^-$=4.07 eq

Organic phase (5088 g) $C_6F_{13}Br$:51.30% $C_{10}F_{21}Br$:48.10% $C_{10}F_{21}I$:0.25%

As in Examples 1 and 2, the degree of conversion of the $C_{10}F_{21}I$ is greater than 99% and the selectivity towards $C_{10}F_{21}Br$ is greater than 99.5%.

We claim:

1. Process for the manufacture of a normally solid perfluoroalkyl bromide comprising:

thermalbromination in the gas phase of a perfluoroalkyl iodide containing 10 or more than 10 carbon atoms to make said normally solid perfluoroalkyl bromide, said thermalbromination being in the presence of a normally liquid perfluoroalkyl bromide containing from 4 to 8 carbon atoms in a quantity sufficient for a mixture of said normally liquid perfluoroalkyl bromide and said normally solid perfluoroalkyl bromide to be liquid at room temperature; and recovering the liquid perfluoroalkyl bromide mixture.

2. Process according to claim 1, wherein the normally liquid perfluoroalkyl bromide is perfluorohexyl bromide or perfluorooctyl bromide.

3. Process according to claim 1, which the $Br_2$/perfluoroalkyl iodide molar ratio is between 0.4 and 2.

4. Process according to claim 1, wherein the reactor is supplied with a homogeneous mixture composed of bromine, the perfluoroalkyl iodide and the normally liquid perfluoroalkyl bromide.

5. Process according to claims 1 for the manufacture of perfluorodecyl bromide from perfluorodecyl iodide $C_{10}F_{21}I$ in the presence of perfluorooctyl bromide $C_8F_{17}Br$, wherein the initial $C_{10}F_{21}I/C_8F_{17}Br$ ratio by weight is between 0.01 and 1.5.

6. Process according to claim 3, wherein the molar ratio is between 0.5 and 0.8.

7. Process according to claim 5, wherein the weight ratio is between 0.1 and 1.

8. Process according to claim 1, wherein the reaction temperature is between 200° and 550° C.

9. Process according to claim 8, wherein the reaction temperature is between 350° and 450° C.

10. Process for the manufacture of a normally solid perfluoroalkyl bromide comprising the steps of:

(a) supplying a reactor with a mixture of bromine ($Br_2$), a perfluoroalkyl iodide containing 10 or more than 10 carbon atoms, and a normally liquid perfluoroalkyl bromide containing from 4 to 8 carbon atoms;

(b) said bromine and said perfluoroalkyl iodide being supplied to said reactor in a $Br_2$/perfluoroalkyl iodide molar ratio of between 0.4 and 2;

(c) operating said reactor under reaction conditions for thermalbromination in the gas phase of said perfluoroalkyl iodide to make said normally solid perfluoroalkyl bromide;

(d) said normally liquid perfluoroalkyl bromide being present in said reactor in a quantity sufficient for a mixture of said normally liquid perfluoroalkyl bromide and said normally solid perfluoroalkyl bromide made in step (c) to be transportable in liquid form at room temperature;

(e) cooling the reaction products of said reactor;

(f) treating the cooled reaction products with a reducing agent to reduce any formed iodine and any unreacted $Br_2$;

(g) separating the mixture of said normally liquid perfluoroalkyl bromide and said normally solid perfluoroalkyl bromide into (i) an upper aqueous phase including iodide and bromide ions, and (ii) a lower organic phase including said normally liquid perfluoroalkyl bromide, said normally solid perfluoroalkyl bromide and any unreacted amount of said perfluoroalkyl iodide;

(h) neutralizing the lower organic phase with an alkaline agent; and (i) distilling the neutralized lower organic phase of step (h) to recover the normally solid perfluoroalkyl bromide.

11. Process according to claim 10 wherein the mixture of step (a) is a homogeneous mixture.

12. Process according to claim 10 wherein the normally solid perfluoroalkyl bromide is perfluorodecyl bromide.

13. Process according to claim 10 wherein the normally liquid perfluoroalkyl bromide is perfluorohexyl bromide or perfluoroctyl bromide.

14. Process according to claim 10 wherein the reaction conditions for thermalbromination in the gas phase of said perfluoroalkyl iodide in step (c) are a temperature from 200° C. to 550° C., a contact time of between 1.0 second and 2.0 minutes, and a pressure for maintaining the thermalbromination reaction in the gas phase.

15. Process according to claim 10 wherein the reaction conditions for thermalbromination in the gas phase of said perfluoroalkyl iodide in step (c) are a temperature from 350° C. to 450° C., a contact time of between 5.0 second and 60.0 seconds, and a pressure for maintaining the thermalbromination reaction in the gas phase.

16. Process according to claim 14 wherein said perfluoroalkyl iodide is perfluorodecyl iodide ($C_{10}F_{21}I$) and said normally liquid perfluoroalkyl bromide is perfluorooctyl bromide ($C_8F_{17}Br$); and wherein the initial $C_{10}F_{21}I/C_8F_{17}Br$ ratio by weight is between 0.01 and 1.5.

17. Process according to claim 15 wherein said perfluoroalkyl iodide is perfluorodecyl iodide ($C_{10}F_{21}I$) and said normally liquid perfluoroalkyl bromide is perfluorooctyl bromide ($C_8F_{17}Br$); wherein the initial $C_{10}F_{21}I/C_8F_{17}Br$ ratio by weight is between 0.1 and 1.0.

18. Process according to claim 16 wherein the $Br_2$/perfluoroalkyl iodide molar ratio is between 0.4 and 2.0.

19. Process according to claim 17 wherein the $Br_2$/perfluoroalkyl iodide molar ratio is between 0.5 and 0.8.

20. Process according to claim 11 wherein the mixture of step (a) is maintained at a temperature of between 25° C. and 40° C.

21. Process for the manufacture of a normally solid perfluoroalkyl bromide comprising:

thermalbromination with bromine in the gas phase of a perfluoroalkyl iodide containing 10 or more than 10 carbon atoms to make said normally solid perfluoroalkyl bromide, said thermalbromination being in the presence of a normally liquid perfluoroalkyl bromide containing from 4 to 8 carbon atoms in a quantity sufficient for a mixture of said normally liquid perfluoroalkyl bromide and said normally solid perfluoroalkyl bromide to be liquid at room temperature; and recovering the liquid perfluoroalkyl bromide mixture.

* * * * *